(12) United States Patent
Kiedrowski

(10) Patent No.: US 10,786,142 B2
(45) Date of Patent: Sep. 29, 2020

(54) SURGICAL INSTRUMENT HAVING WORKING CHANNELS, EACH HAVING A PROFILE EDGE

(71) Applicant: OLYMPUS WINTER & IBE GMBH, Hamburg (DE)

(72) Inventor: Gregor Kiedrowski, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 412 days.

(21) Appl. No.: 15/825,723

(22) Filed: Nov. 29, 2017

(65) Prior Publication Data
US 2018/0078125 A1 Mar. 22, 2018

Related U.S. Application Data

(63) Continuation of application No. PCT/EP2016/062744, filed on Jun. 6, 2016.

(30) Foreign Application Priority Data

Jun. 22, 2015 (DE) .......................... 10 2015 211 424

(51) Int. Cl.
*A61B 1/012* (2006.01)
*A61B 1/018* (2006.01)
(Continued)

(52) U.S. Cl.
CPC .............. *A61B 1/012* (2013.01); *A61B 1/018* (2013.01); *A61B 1/055* (2013.01); *A61B 1/307* (2013.01);
(Continued)

(58) Field of Classification Search
CPC ......... A61B 1/012; A61B 1/015; A61B 1/018; A61B 1/307; A61B 1/00071;
(Continued)

(56) References Cited

U.S. PATENT DOCUMENTS 4,630,598 A 12/1986 Bonnet
4,759,348 A * 7/1988 Cawood ............. A61B 1/00147
600/102
(Continued)

FOREIGN PATENT DOCUMENTS

DE 3916288 A1 11/1989
DE 10129990 A1 1/2003
(Continued)

OTHER PUBLICATIONS

International Search Report dated Aug. 11, 2016 received in PCT/EP2016/062744.
(Continued)

*Primary Examiner* — John P Leubecker
(74) *Attorney, Agent, or Firm* — Scully, Scott & Murphy & Presser, P.C.

(57) ABSTRACT

A surgical instrument, such as an ureteroscope. The surgical instrument including an elongated shaft tube with at least two working channels arranged in an interior of the shaft tube. In at least a distal end area of the shaft tube, the at least two working channels, in cross-section, each have a profile edge.

11 Claims, 1 Drawing Sheet

(51) Int. Cl.
  *A61B 1/307* (2006.01)
  *A61B 1/055* (2006.01)
  *A61B 1/00* (2006.01)
  *A61B 18/26* (2006.01)

(52) U.S. Cl.
  CPC ....... *A61B 1/00071* (2013.01); *A61B 1/00165* (2013.01); *A61B 1/00195* (2013.01); *A61B 18/26* (2013.01)

(58) Field of Classification Search
  CPC ...... A61B 1/00064; A61B 2018/00166; A61B 2017/00234; A61B 2017/00238
  USPC .................................................. 600/128–130
  See application file for complete search history.

(56) References Cited

U.S. PATENT DOCUMENTS

| | | | | |
|---|---|---|---|---|
| 5,131,382 A | * | 7/1992 | Meyer | A61B 1/042 600/104 |
| 5,169,568 A | * | 12/1992 | Ainger, III | A61B 1/015 264/1.25 |
| 5,199,417 A | * | 4/1993 | Muller | A61B 1/07 600/128 |
| 5,320,091 A | * | 6/1994 | Grossi | A61B 1/00135 600/104 |
| 5,782,838 A | * | 7/1998 | Beyar | A61B 1/307 623/1.11 |
| 6,328,730 B1 | * | 12/2001 | Harkrider, Jr. | A61B 17/3421 600/130 |
| 6,358,200 B1 | * | 3/2002 | Grossi | A61B 1/12 600/156 |
| 6,878,106 B1 | * | 4/2005 | Herrmann | A61B 1/00073 600/104 |
| 2001/0056222 A1 | * | 12/2001 | Rudischhauser | A61B 1/00135 600/130 |
| 2003/0125607 A1 | * | 7/2003 | Boebel | A61B 1/00105 600/136 |
| 2005/0085692 A1 | * | 4/2005 | Kiehn | A61B 1/00105 600/130 |
| 2006/0129030 A1 | | 6/2006 | Dehmel | |
| 2007/0250038 A1 | | 10/2007 | Boulais | |
| 2007/0282305 A1 | * | 12/2007 | Goldfarb | A61B 1/0014 604/528 |
| 2008/0071269 A1 | * | 3/2008 | Hilario | A61B 1/00154 606/50 |
| 2008/0208001 A1 | | 8/2008 | Hadani | |
| 2010/0160729 A1 | | 6/2010 | Smith et al. | |
| 2010/0268023 A1 | | 10/2010 | Campo et al. | |
| 2011/0118544 A1 | | 5/2011 | Adams et al. | |
| 2012/0078038 A1 | * | 3/2012 | Sahney | A61B 17/3421 600/104 |
| 2012/0232526 A1 | | 9/2012 | Boulais | |
| 2015/0351617 A1 | | 12/2015 | Simchony et al. | |
| 2016/0249784 A1 | * | 9/2016 | Bresco Torras | A61B 1/00195 600/128 |
| 2016/0250445 A1 | | 9/2016 | Boulais | |

FOREIGN PATENT DOCUMENTS

| | | |
|---|---|---|
| DE | 102004059255 B3 | 5/2006 |
| DE | 102010054422 A1 | 6/2012 |
| EP | 2229871 A1 | 9/2010 |
| JP | H08-506259 A | 7/1996 |
| JP | H11-342107 A | 12/1999 |
| JP | 2000-166936 A | 6/2000 |
| JP | 2001-046335 A | 2/2001 |
| JP | 2007-503277 A | 2/2007 |
| JP | 2012-101121 A | 5/2012 |
| WO | 2007124210 A1 | 11/2007 |
| WO | 2014111946 A1 | 7/2014 |

OTHER PUBLICATIONS

Japanese Office Action dated Jan. 28, 2020 in Japanese Patent Application No. 2017-566750.
Japanese Office Action dated May 14, 2019 in Japanese Patent Application No. 2017-566750.

\* cited by examiner

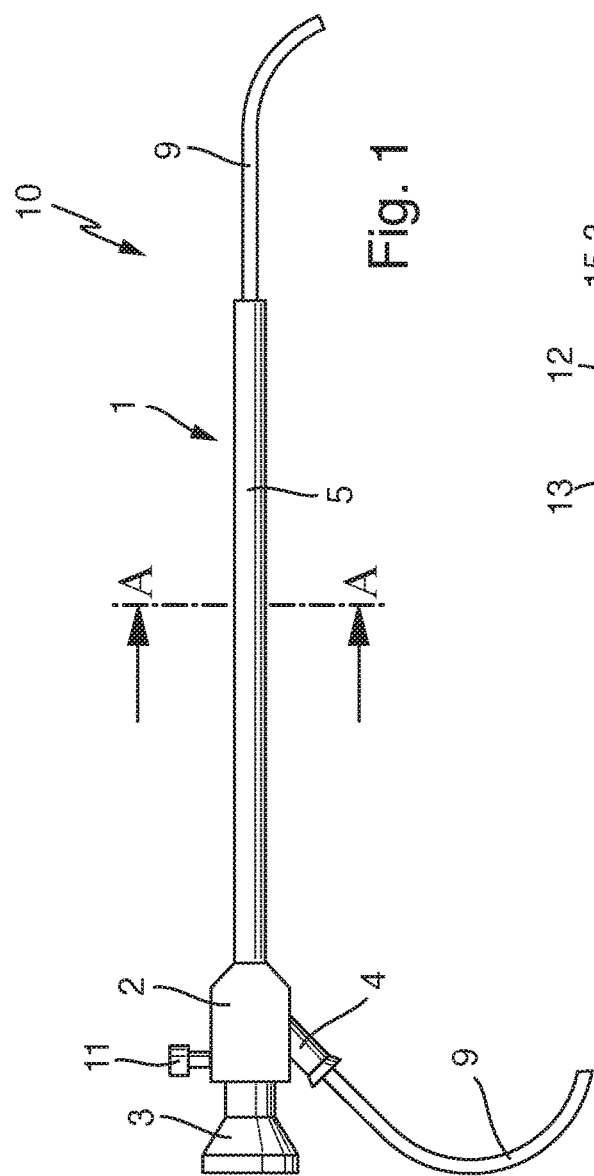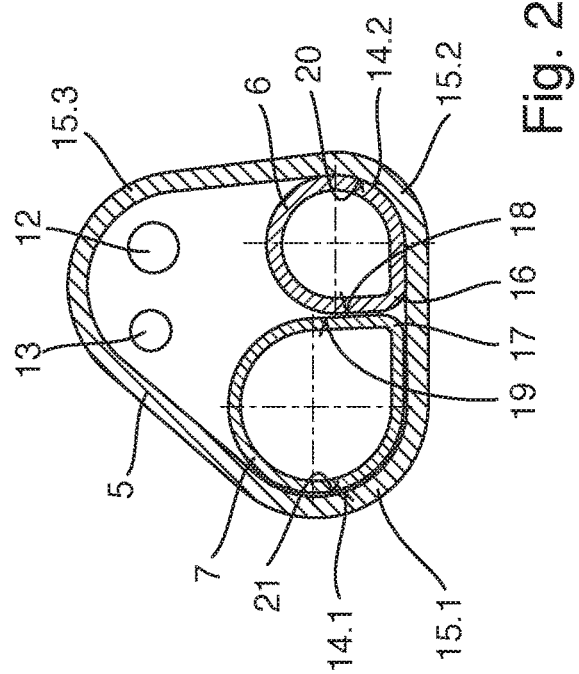

SURGICAL INSTRUMENT HAVING WORKING CHANNELS, EACH HAVING A PROFILE EDGE

CROSS-REFERENCE TO RELATED APPLICATION

The present application is a continuation of PCT/EP2016/062744 filed on Jun. 6, 2016, which is based upon and claims the benefit to DE 10 2015 211 424.4 filed on Jun. 22, 2015, the entire contents of each of which are incorporated herein by reference.

BACKGROUND

Field

The present application relates to a surgical instrument, such as an ureteroscope, with an elongated shaft tube, which can be rigid, for receiving at least two working channels and with at least two working channels arranged in the shaft tube.

Prior Art

In the field of urology, ureteroscopes are used for endoscopic work in the ureter and in the pelvis of the kidney. In order to reach this area endoscopically, the ureteroscope is pushed in from outside through the urethra into the bladder; from here, it is inserted through the ostium (mouth of the ureter with cover flap) into the ureter and is pushed in this up to the operative area, for example up to a stone or a narrowing in the ureter or respectively up to the pelvis of the kidney.

The shaft tube of the ureteroscope typically has a length of at least approximately 400 mm. Since the ureter, including the ostium are very narrow, the shaft diameter should not be larger than approximately 3 to 4 mm. This results in an extremely long and thin configuration of the shaft tube.

The shaft tube of an ureteroscope should be rigid, in order to enable the guidance of the distal end from the proximal end, including during the difficult insertion into the ostium. The shaft tube is thus generally rigid and has an exterior metal tube, which gives it the necessary rigidity and which surrounds the inner-lying parts of the shaft tube in a liquid-impermeable manner.

Inside the shaft tube, at least one observation device is provided as well as optical fibers for illumination and working channels, which enable the insertion of instruments like catheters, forceps, kidney stone retrieval devices, lithotripters (kidney stone fragmenting devices) etc.

For example, a ureteroscope is described in DE 10 2004 059 255 B3.

Moreover, ureteroscopes with two working channels are also known so that instruments can be inserted through two working channels, whereby the versatility and flexibility is increased during the use of ureteroscopes.

SUMMARY

An object is to improve the handling of ureteroscopes with working channels in a simple manner.

Such object can be solved by a surgical instrument, such as an ureteroscope, with an elongated shaft tube, which can be rigid, for receiving at least two working channels and with at least two working channels arranged in the shaft tube, wherein, at least in the distal end area of the shaft tube, the working channels in cross-section each comprise a profile edge or a profile nose.

Through the formation of the two working channels arranged in the shaft tube of the surgical instrument with a profile nose or profile edge in cross-section, such as on the distal end of the shaft tube, the working channels can comprise a non-round, i.e. non-circular or non-oval, geometry so that they are adjusted to the inner contour of the shaft tube in an area, wherein the cross-section of the distal inner contour of the shaft tube can be formed like a polygon. The inner contour and the outer contour of the shaft tube can comprise a polygonal shape or a polygonal profile in cross-section, wherein the polygonal shape or the polygonal profile can comprise rounded corners.

The working channels can be each formed with a profile edge or a profile nose so that the working channels are arranged in a space-saving manner with a simultaneous reduction in the size of the intermediate spaces that may need to be filled between the working channels as well as between the working channels and the shaft tube.

The working channels can each comprise a contact surface facing the other, such as planar and/or complementary in shape, working channel, whereby the intermediate space as well as the distance between the two working channels can be decreased. Wherein the contact surfaces of the working channels facing each other can work together in a manner that is complementary in shape. The contact surfaces facing each other can be formed in a planar manner.

Moreover, the contact surfaces of the working channels facing each other can be interconnected, such as by being soldered together. The intermediate space between the working channels can be filled in a fluid-impermeable manner through the connection or respectively soldering of the working channels. The working channels can be made of metal for the soldering of the working channels.

The working channels can each comprise a lumen, wherein the lumina of the working channels can be different.

At least in the distal end area, the shaft tube can comprise a polygonal shape in cross-section or can be formed in a polygonal shape manner. The shaft tube of the surgical instrument, such as the ureteroscope, can be formed in a rigid manner, wherein it is provided in a further design that the shaft tube, in which the two working channels are arranged, can have, in cross-section, a polygonal shape over the entire length or can be formed like a polygonal shape.

The shaft tube can have a triangular polygonal shape in cross-section. The triangular polygonal shape can have rounded edges. Furthermore, the polygonal shape can be asymmetrical in cross-section.

Moreover, inside the shaft tube can comprise a shaft tube contact surface, such as being in cross-section with a planar shaft tube contact surface section and/or a bent shaft tube contact surface section, for the at least two working channels. The working channels, each of which can comprise a profile edge or a profile nose, can be arranged in the shaft tube on the shaft tube contact surface, whereby intermediate spaces as well as the distance between the working channels and the inside of the shaft tube can be reduced in size.

The working channels can each comprise a working channel bearing surface facing the shaft tube contact surface, wherein the outer working channel bearing surfaces of the working channels can be connected, such as being soldered, with the shaft tube contact surfaces, such as each with a shaft tube contact surface section for a working channel bearing surface. Due to on one hand the working channels may be interconnected, such as being soldered, via their interfacing contact surfaces and on the other hand each of the working channels can comprise a working channel bearing surface facing the inside of the shaft tube and the working channel bearing surfaces of the working channels can be connected with the shaft tube contact surface, there can be no hollow spaces in the arrangement of the working channels in the shaft tube between the working channels and the shaft tube. The working channels can be formed such that each working channel is connected with a planar shaft tube contact surface section and a curved shaft tube contact surface section, whereby one or more working channels is associated with a rounded corner of the shaft tube with polygonal cross-section.

The working channels and the shaft tube can be respectively advantageously formed as metal tubes. Moreover, the surgical instrument can be formed as a ureteroscope.

BRIEF DESCRIPTION OF THE DRAWINGS

Further features will become apparent from the description of embodiments together with the claims and the included drawings. Embodiments can fulfill individual characteristics or a combination of several characteristics.

The embodiments are described below, without restricting the general idea using exemplary embodiments with reference to the drawings, wherein we expressly refer to the drawings with regard to the disclosure of all details that are not explained in greater detail in the text.

FIG. 1 schematically illustrates a side view of a ureteroscope;

FIG. 2 schematically illustrates a cross-section through the shaft tube along the line A-A in FIG. 1.

DETAILED DESCRIPTION

In the drawings, the same or similar types of elements and/or parts are provided with the same reference numbers so that a re-introduction is omitted.

FIG. 1 shows schematically a rigid ureteroscope 10. It has a shaft part 1, on the proximal end of which a main body 2 is fastened with eyepiece 3 and insertion part 4. The shaft part 1 has an exterior shaft tube 5 determining the outer periphery.

Two inner working channels 6 and 7 are arranged inside the shaft part 1 (see FIG. 2), through which instruments are inserted. Furthermore, an optical fiber 13 (see FIG. 2) and an optical channel with optics 12 (see FIG. 2) are arranged in the space between the working channels 6 and 7 and the shaft tube 5 so that an image of a lens arranged on the distal end of the shaft part 1 is transmitted to the eyepiece 3.

The working channels 6 and 7 respectively surround a lumen, through which an instrument 9 can be pushed through the insertion part 4 into one of the working channels 6, 7. In the example shown, the instrument 9 is a laser lithotripter, the proximally provided laser generator of which is not shown. Another instrument can also be inserted into the other, free working channel.

The space between the inner working channels 6 and 7 and the shaft tube 5 is filled up among other things with an optical fiber (not shown), which is made e.g. of optical fibers and serves to illuminate the observation field. On the proximal end, the optical fiber is lead out of the main body 2 via an optical fiber connection 11. There, an optical fiber connection channel can be connected to a light source (not shown).

The length of the shaft part 1 of an ureteroscope is for example 400 to 500 mm. The outer diameter of the shaft part 1, i.e. the outer diameter of the outer shaft tube 5, is approximately 4 mm at a maximum.

As can be seen from the schematic representation in FIG. 2, the shaft tube 5 has a triangular polygonal shape in cross-section, wherein the triangular, asymmetrical polygonal shape has rounded corners 15.1, 15.2, 15.3. Optics 12 and an optical fiber 13 are arranged in the shaft tube 5, which extends in the longitudinal direction of the shaft tube 5 from the proximal to the distal end.

The working channels 6, 7 are each formed in cross-section with a profile edge 16 or respectively 17, whereby the cross-sections of the working channels 6 and 7 are teardrop-shaped. The profile edges 16, 17 of the working channels 6, 7 are interfacing and arranged across from each other. Furthermore, the cross-sections of the working channels 6 and 7 thereby comprise interfacing, planar contact surfaces 18 and 19, which are interconnected by soldering or the like. The cross-sections of the working channels 6, 7 only comprise the profile edges 16, 17 in the distal area. The profile edges 16, 17 of the working channels 6, 7 can be formed for example by drifting the cross-sectional shape.

The teardrop shape of the cross-sections of the working channels 6, 7 is adjusted to the respective contour of the corners 15.1, 15.2, in which the working channels are arranged so that the working channels 6, 7 with their outer bearing surfaces 20, 21 for the corners 15.1, 15.2 are each connected or respectively soldered with a shaft tube contact surface 14.1, 14.2 facing the bearing surfaces 20, 21. The shaft tube contact surfaces 14.1, 14.2 comprise both planar shaft tube contact surface sections and curved shaft tube contact surface sections, which are connected with the working channels 6, 7.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

1 Shaft part
2 Main body
3 Eyepiece
4 Insertion part
5 Shaft tube
6 Working channel
7 Working channel
9 Instrument
10 Ureteroscope
11 Fiber-optic connection
12 Lens system
13 Optical fiber
14.1, 14.2 Shaft tube contact surface
15.1, 15.2, 15.3 Corner
16 Profile edge
17 Profile edge
18 Contact surface
19 Contact surface
20 Bearing surface
21 Bearing surface

What is claimed is:
1. A surgical instrument comprising:
an elongated shaft tube; and at least two working channels arranged in an interior of the shaft tube;

wherein, at least in a distal end area of the shaft tube, the at least two working channels, in cross-section, each comprise a profile edge;

the shaft tube comprises a contact surface corresponding to each of the at least two working channels, each contact surface comprising a planar contact surface section and a curved contact surface section; and each of the planar contact surface sections and the curved contact surface sections are interconnected to corresponding surfaces of the at least two working channels by solder.

2. The surgical instrument according to claim 1, wherein one of the at least two working channels comprise a first contact surface facing a second contact surface of the other of the at least two working channels.

3. The surgical instrument according to claim 2, wherein the first and second contact surfaces are planar.

4. The surgical instrument according to claim 2, wherein the first and second contact surfaces are complimentary in shape.

5. The surgical instrument according to claim 2, wherein the first and second contact surfaces are interconnected.

6. The surgical instrument according to claim 5, wherein the first and second contact surfaces are interconnected by being soldered together.

7. The surgical instrument according to claim 1, wherein the first and second working channels each comprise a lumen, wherein a cross-section of the lumen of the first working channel is different in size from a cross-section of the lumen of the second working channel.

8. The surgical instrument according to claim 1, wherein, at least in the distal end area, the shaft tube, in cross-section, is formed in a polygonal shape.

9. The surgical instrument according to claim 8, wherein the shaft tube wherein the polygonal shape is a triangular polygonal shape.

10. The surgical instrument according to claim 1, wherein the at least two working channels and the shaft tube are each formed as metal tubes.

11. An ureteroscope comprising:
an elongated shaft tube; and
at least two working channels arranged in an interior of the shaft tube;
wherein, at least in a distal end area of the shaft tube, the at least two working channels, in cross-section, each comprise a profile edge;
the shaft tube comprises a contact surface corresponding to each of the at least two working channels, each contact surface comprising a planar contact surface section and a curved contact surface section; and
each of the planar contact surface sections and the curved contact surface sections are interconnected to corresponding surfaces of the at least two working channels by solder.

\* \* \* \* \*